United States Patent
Chandrasekar et al.

(10) Patent No.: US 9,662,474 B2
(45) Date of Patent: *May 30, 2017

(54) CATHETER WITH VARIABLE ATTACHMENT MEANS

(71) Applicant: IQ Medical Devices, Belmont, MA (US)

(72) Inventors: N R Chandrasekar, Canton, MA (US); Donald McKay, Belmont, MA (US)

(73) Assignee: IQ Medical Devices, LLC, Belmont, MA (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/047,634

(22) Filed: Oct. 7, 2013

(65) Prior Publication Data

US 2014/0228764 A1    Aug. 14, 2014

Related U.S. Application Data

(63) Continuation of application No. 13/168,383, filed on Jun. 24, 2011, now abandoned, which is a (Continued)

(51) Int. Cl.
*A61M 25/02* (2006.01)
*A61M 25/01* (2006.01)
(Continued)

(52) U.S. Cl.
CPC ........ *A61M 25/02* (2013.01); *A61M 25/0108* (2013.01); *A61B 17/04* (2013.01);
(Continued)

(58) Field of Classification Search
CPC .......... A61M 25/02; A61M 2025/0206; A61M 2025/0253; A61M 2025/0286; A61B 17/04
See application file for complete search history.

(56) References Cited

U.S. PATENT DOCUMENTS 3,159,161 A   12/1964  Ness
3,176,690 A    4/1965  H'Doubler
(Continued)

FOREIGN PATENT DOCUMENTS

CA        1 231 018        1/1988

OTHER PUBLICATIONS

Banerjee, et al. (2007) "Recommended Method of Attachment of Nasogastric Tubes" Ann. R. Coll. Surg. Engl. 89(5): 529-530 (Abstract only).
(Continued)

*Primary Examiner* — Bradley Osinski
(74) *Attorney, Agent, or Firm* — Goodwin Procter LLP

(57) ABSTRACT

The invention relates to a design for securing tubes, catheters, drains, or other tubular medical devices within the body of a mammal, for example a human, and methods of securing same. The invention includes a first tubular body and at least one second tubular body. The first tubular body includes an outer surface, an inner surface defining a lumen extending longitudinally at least partially through a length of the tubular body, a wall at least partially defined by the outer surface and the inner surface, and a longitudinal axis. The at least one second tubular body includes an outer surface, an inner surface defining a lumen extending longitudinally through the second tubular body, and a wall at least partially defined by the outer surface and the inner surface. The second tubular body is disposed through the wall of the first tubular body transversely to the longitudinal axis.

19 Claims, 13 Drawing Sheets

Related U.S. Application Data continuation of application No. 11/754,043, filed on May 25, 2007, now Pat. No. 7,967,788.

(51) Int. Cl.
 *A61B 17/04* (2006.01)
 *A61M 25/04* (2006.01)

(52) U.S. Cl.
 CPC .......... *A61B 17/0482* (2013.01); *A61M 25/04* (2013.01); *A61M 2025/0206* (2013.01); *A61M 2025/0226* (2013.01); *A61M 2025/0253* (2013.01); *A61M 2025/0286* (2013.01); *A61M 2210/0618* (2013.01)

(56) References Cited

U.S. PATENT DOCUMENTS

| | | |
|---|---|---|
| 3,777,761 A | 12/1973 | Sheridan |
| 3,862,635 A | 1/1975 | Harautuneian |
| 3,972,321 A | 8/1976 | Proctor |
| 4,230,110 A | 10/1980 | Beroff |
| 4,367,769 A | 1/1983 | Bain et al. |
| 4,480,639 A | 11/1984 | Peterson et al. |
| 4,483,337 A | 11/1984 | Clair |
| 4,527,559 A | 7/1985 | Roxburg et al. |
| 4,569,348 A | 2/1986 | Hasslinger |
| 4,607,635 A | 8/1986 | Heyden |
| 4,637,389 A | 1/1987 | Heyden |
| 4,642,101 A | 2/1987 | Krolikowski et al. |
| 4,742,824 A | 5/1988 | Payton et al. |
| 4,778,448 A | 10/1988 | Meer |
| 4,795,442 A | 1/1989 | Traflet |
| 4,823,789 A | 4/1989 | Beisang, III |
| 4,932,943 A | 6/1990 | Nowak |
| 5,038,778 A | 8/1991 | Lott |
| 5,101,822 A | 4/1992 | Kimmel |
| 5,105,807 A | 4/1992 | Kahn et al. |
| 5,156,641 A | 10/1992 | White |
| 5,188,609 A | 2/1993 | Bayless et al. |
| 5,295,480 A | 3/1994 | Zemo |
| 5,354,132 A | 10/1994 | Young et al. |
| 5,509,902 A | 4/1996 | Raulerson |
| 5,546,938 A | 8/1996 | McKenzie |
| 5,619,875 A | 4/1997 | Lahaussois |
| 5,628,786 A | 5/1997 | Banas et al. |
| 5,655,518 A | 8/1997 | Burden |
| 5,682,881 A | 11/1997 | Winthrop et al. |
| 5,700,252 A | 12/1997 | Klingenstein |
| 5,700,286 A | 12/1997 | Tartaglia et al. |
| 5,735,272 A | 4/1998 | Dillon et al. |
| 5,752,511 A | 5/1998 | Simmons et al. |
| 5,824,061 A | 10/1998 | Quijano et al. |
| 5,868,132 A | 2/1999 | Winthrop et al. |
| 5,871,536 A | 2/1999 | Lazarus |
| 6,036,699 A | 3/2000 | Andreas et al. |
| 6,045,536 A | 4/2000 | Meier et al. |
| 6,206,915 B1 | 3/2001 | Fagan et al. |
| 6,298,850 B1 | 10/2001 | Argraves |
| 6,328,038 B1 | 12/2001 | Kessler et al. |
| 6,352,561 B1 | 3/2002 | Leopold et al. |
| 6,463,927 B1 | 10/2002 | Pagan et al. |
| 6,464,668 B1 | 10/2002 | Pace |
| 6,536,437 B1 | 3/2003 | Dragisic |
| 6,565,537 B2 | 5/2003 | Tollini |
| 6,669,712 B1 | 12/2003 | Cardoso |
| 6,837,237 B2 | 1/2005 | Kirn |
| 6,863,066 B2 | 3/2005 | Ogle |
| 6,899,102 B1 | 5/2005 | McGlothen |
| 6,976,952 B1 | 12/2005 | Maini et al. |
| 6,994,088 B2 | 2/2006 | Briggs, III |
| 7,000,611 B2 | 2/2006 | Klemperer |
| 7,195,018 B1 | 3/2007 | Goldstein |
| 2002/0143389 A1 | 10/2002 | St. Pierre |
| 2003/0083646 A1 | 5/2003 | Sirhan et al. |
| 2003/0212448 A1 | 11/2003 | Smith |
| 2004/0193092 A1 | 9/2004 | Deal |
| 2005/0103332 A1 | 5/2005 | Gingles et al. |
| 2005/0236001 A1 | 10/2005 | Williams |
| 2006/0025848 A1 | 2/2006 | Weber et al. |
| 2006/0289011 A1 | 12/2006 | Helsel |

OTHER PUBLICATIONS

Burns, et al. (1995) "Comparison of nasogastric tube securing methods and tube types in medical intensive care patients" Am. J. Crit. Care 4(3): 198-203 (abstract only).

Pancorbo-Hidalgo, et al. (2001) "Complications associated with enteral nutrition by nasogastric tube in an internal medicine unit" J. Clin. Murs. 10(4): 482-90 (Abstract only).

Petroianu, et al. (2010) "Fastening technique of nasogastric and nasoenteric tubes" Rev. Col. Bras. Cir. 37(1): 70-1 (Abstract only).

International Search Report and Written Opinion for PCT/US2008/064466, mailed on Mar. 12, 2009 (15 pages).

International Preliminary Report on Patentability for PCT/US2008/064466, dated Dec. 1, 2009 (includes Written Opinion mailed on Mar. 3, 2009) (10 pages).

European Office action for 08769583.9 date Feb. 18, 2011 (5 pages).

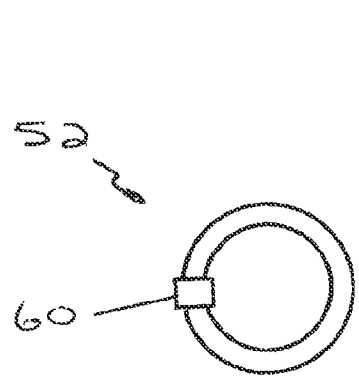
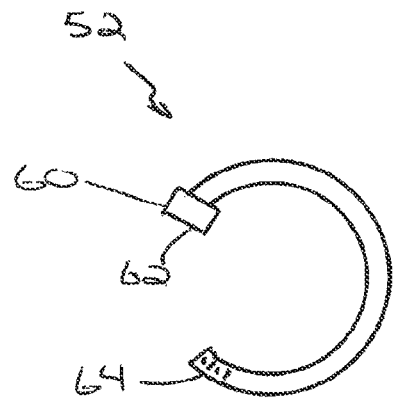
FIG. 9A  FIG. 9B
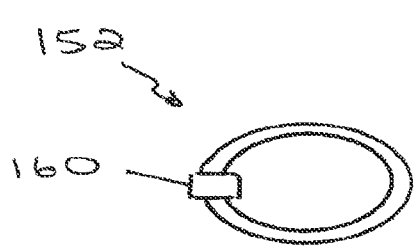
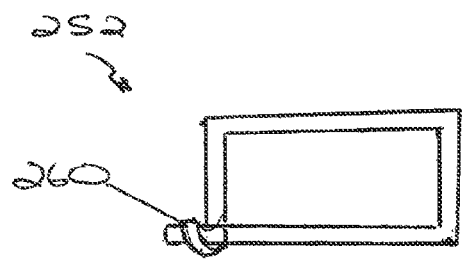
FIG. 9C  FIG. 9D
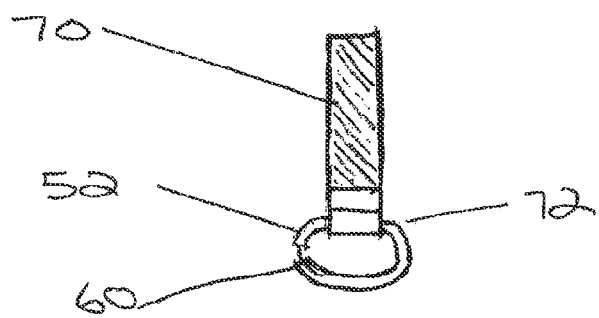
FIG. 10

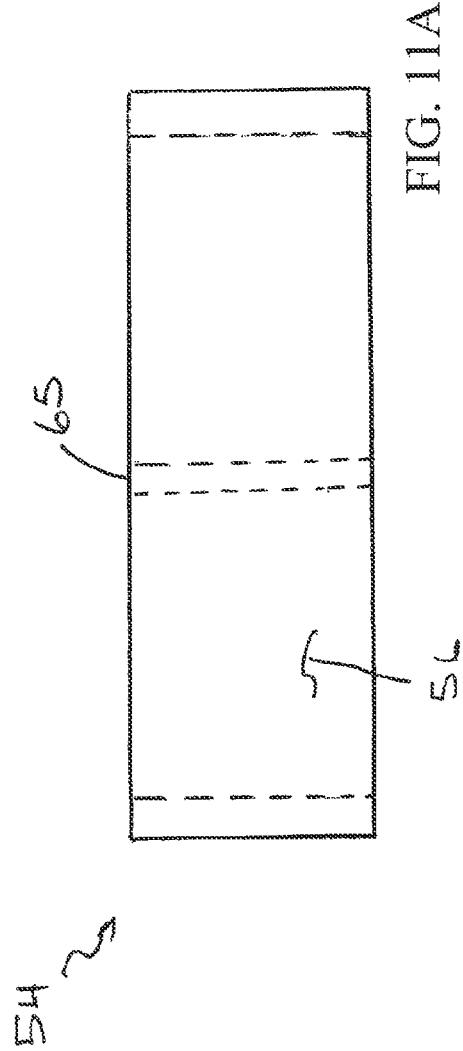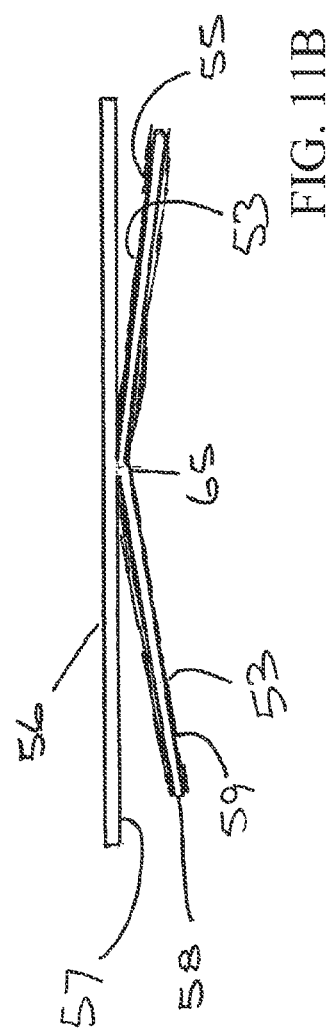

CATHETER WITH VARIABLE ATTACHMENT MEANS

RELATED APPLICATION

This application is a continuation of U.S. application Ser. No. 13/168,383, filed Jun. 24, 2011, which is a continuation of U.S. application Ser. No. 11/754,043 (now U.S. Pat. No. 7,967,788), filed May 25, 2007, the entire disclosures of which are incorporated by reference herein.

FIELD OF THE INVENTION

This invention relates generally to means for securing catheters or other tubular medical devices in a mammalian body, and more particularly to catheters with variable attachment means.

BACKGROUND

Every day thousands of tubes, drains, and catheters are placed in and removed from the bodies of humans. All of these tubes, drains, and catheters have at least one significant drawback. It is very easy for them to become displaced, twisted, or dislodged, or to simply fall out. The complications of this occurrence can be serious as a patient may suffer aspiration pneumonia, aspiration pneumonitis, peritonitis, pneumothorax, or even death. An operation, or at least trips to an X-ray suite, may be necessary for reinsertion of the tube, drain, or catheter. In some cases, the patient may not be a candidate for reoperation, and suffering or even death may occur. In addition, this problem can result in large additional expense to the healthcare industry and the consumer. For example, for patients on chronic enteral feeding at home or in a nursing home, tube displacement typically requires a trip to the hospital for replacement of the tube, thereby increasing the risks to the patient while incurring significant costs.

Furthermore, disfigurement, such as nasal tip necrosis or other areas of skin and subcutaneous necrosis, may occur and require replacement of the tube in a different location. Because many tubes are secured by multiple layers of adhesive tape, and possibly medical dressings, constriction angulation, displacement, or other obvious complications may not be observed until it is too late. Tape, which is frequently used to secure tubes, catheters, and drains, is messy and hard to use, in particular with a gloved hand, possibly exposing a care giver to harmful bodily fluids. Besides being inefficient, tape causes perspiration and irritation to the patient's skin, such as a rash or ulcer.

A specific drawback with respect to adhesive tape applies to securing a nasogastric tube for drainage, even if for only a short period of time. It is difficult to stabilize the tube on the outside of the nose with adhesive tape, which is typically used to secure the tube to the nasal skin. If the tape is applied too tightly, the tube may irritate the skin of the inside of the nostril. If the tape is poorly applied, it may work loose from the nasal skin or its purchase on the tube itself and the position of the tube may change, or the tube may simply fall out. Additionally, blistering or maceration of the underlying skin can occur. The tape often needs to be changed frequently, thereby creating opportunities for accidents to occur.

Currently several holders for external tubes, drains and catheters are available; however, they tend to be bulky and cumbersome to use. In addition, the holders themselves have to be secured to the tube, catheter, or drain and anchored to the patient, which generates problems with securing them. For example, the holders may cause external compression on the tubes, catheters, and drains that they are holding, thereby changing the dynamics and dimensions of the tubes, catheters, and drains and compromising their function, for example impeding or completely obstructing drainage. The holders are not universally practical for all situations involving tubes, catheters and drains, for example, the holders can not be used internally. As such, the holders are not widely used. Currently there is no method of securing a tube internally, i.e., in the small bowel.

Therefore, there is a need of a method to reliably secure catheters, tubes, and drains in or on the mammalian body and for catheters, tubes, and drains with means for variably and reliably securing them in or to the mammalian body regardless of the catheter's size or shape, the part of the body needed to secure the catheter, or the location of the part of the body to which the catheter is secured.

SUMMARY

The present invention is generally directed to a universal design for securing tubes, catheters, drains, cannulas, stents, or other tubular medical devices (collectively "catheters"), either hollow or solid, that are used for, for example, draining bodily fluids or introducing materials into the human body. For example, a catheter in accordance with the invention can apply to chest tubes, feeding tubes, drainage catheters, drug delivery devices, and the like. The catheters can reside externally and/or internally to the human body and can be temporarily or permanently secured to the patient.

The catheter incorporates in its design transverse perforations in its tubular body. These perforations can run the length of the catheter or a segment thereof, giving the medical personnel multiple options with respect to securing the catheter. These perforations extend through a wall of the catheter and do not communicate with a lumen defined by the tubular body. In some cases, the perforations are micro-tubes that may intersect with the lumen. Because the micro-tubes include outer surfaces, the lumens of the micro-tubes remain fluidically isolated from the lumen of the catheter, as the wall of the catheter will seal against the outer surfaces of the micro-tubes. A suture, thread, loop, or ring (collectively "sutures") can be passed through one or more perforations, thereby securing (e.g., anchoring and/or suspending) the catheter in place to, for example, adjacent tissue (e.g., skin). The suture or other means for securing the catheter do not interfere with the biomechanics of the catheter itself. The catheter may be secured either externally or internally, for example to the bowel or bladder. Moreover, the perforations may act as a ready marker of the catheter's position. Anchoring may be permanent or temporary and a minimal dressing may be used. Bulky layers of tape or dressing are eliminated.

Generally, catheters in accordance with the invention can be secured at multiple locations and orientations to accommodate variations in the anatomy of a patient. Typically, the catheters can be of any of the types used for medical applications. The catheters can include one or more central lumens and may include valving or other openings, as necessary to suit a particular application. Various examples of catheters and other tubular medical devices can be found, for example, in U.S. Pat. No. 4,549,879, U.S. Pat. No. 4,753,640, U.S. Pat. No. 6,939,320, U.S. Pat. No. 6,997,899, U.S. Pat. No. 7,041,139, and U.S. Pat. No. 6,436,077, the entire disclosures of which are hereby incorporated herein by reference.

In one aspect, the invention relates to a catheter having a tubular body that includes an outer surface, an inner surface, a wall at least partially defined by the outer surface and the inner surface, and a longitudinal axis. The inner surface defines a lumen extending longitudinally at least partially through a length of the tubular body. The catheter also includes at least one opening extending through the wall substantially transversely to the longitudinal axis. The at least one opening is in fluidic isolation from the lumen.

In another aspect, the invention relates to a catheter having a first tubular body and at least one second tubular body. The first tubular body includes an outer surface, an inner surface defining a lumen extending longitudinally at least partially through a length of the tubular body, a wall at least partially defined by the outer surface and the inner surface, and a longitudinal axis. The at least one second tubular body includes an outer surface, an inner surface defining a lumen extending longitudinally through the second tubular body, and a wall at least partially defined by the outer surface and the inner surface. The second tubular body is disposed through the wall of the first tubular body transversely to the longitudinal axis.

In various embodiments of the foregoing aspects, an outer cross-sectional dimension of the second tubular body is less than a thickness of the wall of the first tubular body. The cross-sectional dimension of the inner surface of the second tubular body can have a diameter of about 0.005 mm to about 8.0 mm, preferably about 0.01 mm to about 6.0 mm, and more preferably about 0.1 to about 5.0 mm. The catheter can also include a plurality of second tubular bodies disposed through the wall of the first tubular body. The plurality of second tubular bodies can be evenly spaced along an overall length of the first tubular body, and a first portion of the plurality of second tubular bodies can be radially disposed about a central longitudinal axis of the first tubular body from a second portion of the plurality of the second tubular bodies. In one embodiment, the first and second portions of the second tubular bodies are disposed at opposing sides of the catheter. In other words, the first portion of the second tubular bodies are radially disposed about 180 degrees from the second portion of the second tubular bodies. The catheter can include a radio-opaque material disposed therein to aid in the imaging and placement of the catheter. The catheter can also include a series of markings (e.g., printed measurements or color-coded bands) disposed on the outer surface of the first tubular body. In various embodiments of the catheter, the first tubular body can include a second inner surface defining a second lumen extending longitudinally at least partially through the length of the tubular body. Additional inner surfaces and lumens are contemplated and within the scope of the invention.

Additionally, the outer surface of the first tubular body and the inner surface of the first tubular body can be eccentric, as can be the outer surface and the inner surface of the second tubular bodies. The catheter, lumens, and the inner and outer surfaces of the tubular bodies can have cross-sectional shapes selected from the group consisting of circular, elliptical, polygonal, and combinations thereof. The first tubular body can be made of a material selected from the group consisting of polyurethane, silicones, polyethylenes, nylons, polyesters and polyester elastomers. The second tubular body can be made of a material selected from the group consisting of stainless steel, titanium, polyurethane, silicones, polyethylenes, nylons, polyesters and polyester elastomers.

In additional embodiments, the catheter can include a fastening mechanism for securing the catheter to a mammalian body. The catheter fastening mechanism can include a ring having an open configuration and a closed configuration and a fastening strap for coupling the ring to the mammalian body. The ring can be adapted to pass through at least one of the second tubular bodies or other opening through a wall of the catheter. The ring can have a shape of, for example, round, oval, or polygonal. The ring can be locked in the closed configuration. The fastening strap can include a first layer of material adapted for attachment to a portion of the mammalian body and a second layer of material adapted to secure at least a portion of the ring to the fastening strap. The first and second layers can be attached at their respective ends to trap the ring between the two layers. In addition, the fastening strap can include an adhesive and/or a hook and loop type fastener, such as the Velcro® brand sold by Velcro Industries B.V. For example, the first layer of material can be secured to the mammalian body with an adhesive and the second layer of material can be secured to the first layer of material by the hook and loop type fastener to secure the ring therebetween.

In another aspect, the invention relates to a catheter fastening mechanism for securing a catheter to a mammalian body. The mechanism includes a ring having an open configuration and a closed configuration and a fastening strap for coupling the ring to the mammalian body. The ring can be adapted to pass through an opening through a wall of the catheter. The ring can have a shape of, for example, round, oval, or polygonal. The ring can be locked in the closed configuration. The fastening strap can include a first layer of material adapted for attachment to a portion of the mammalian body and a second layer of material adapted to secure at least a portion of the ring to the fastening strap. The fastening strap can include an adhesive and/or a hook and loop type fastener.

In another aspect, the invention relates to a method of manufacturing a catheter. The method includes the steps of extruding a first tubular body comprising an outer surface, an inner surface defining a lumen extending longitudinally at least partially through a length of the first tubular body, a wall at least partially defined by the outer surface and the inner surface; and inserting a second tubular body through the wall of the first tubular body proximate the point of extrusion prior to the first tubular body hardening, the second tubular body inserted transversely to the direction of extrusion.

In various embodiments of the method, the step of inserting a second tubular body includes inserting a plurality of second tubular bodies spaced along a length of the first tubular body, as the first tubular body is extruded. The plurality of second tubular bodies can be disposed radially about a central longitudinal axis of the first tubular body. In one embodiment, an outer cross-sectional diameter of the second tubular body is less than a thickness of the wall of the first tubular body.

In another aspect, the invention relates to a method of securing a catheter in a mammal. The method includes inserting at least a portion of a catheter in accordance with one of the previous aspects of the invention into a predetermined region of the mammal. The catheter is inserted such that at least one opening extending through the wall or second tubular body is located outside the predetermined region. The method also includes the step of passing a suture through the opening or second tubular body and securing the suture to an anatomical structure disposed outside the predetermined region.

In a particular embodiment where at least a portion of the catheter is to be secured within the body, the catheter can be secured at multiple points along the length of a viscera organ (e.g., small bowel or bladder) prior to the point of entry of the catheter into the organ, such that the catheter is oriented substantially parallel to and contours to the shape of the organ. Such an arrangement allows the catheter to move with the organ. In a similar embodiment, the catheter can be secured within or between the outer layers of tissue (e.g., muscle) of the organ. The catheter can be secured at multiple locations within a tunnel formed by the layers of tissue relative to the point of entry of the catheter into the organ. For example, the catheter can be sutured to the layers of tissue at multiple points along the tunnel formed by the layers of tissue. In addition, the catheter can be secured between multiple organ systems.

In various embodiments of the foregoing aspect of the invention, the predetermined region is any body cavity or organ system, including pleural, pericardial, or abdominal cavities, trachea, bronchi, gastrointestinal tract from the upper esophagus to the anus, kidneys, ureters, and bladder. The anatomical structure can be at least one of skin and tissue spaced apart from the predetermined region.

These and other objects, along with the advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 9A and 9B are schematic plans views of a ring for use in a catheter fastening mechanism in accordance with one embodiment of the invention in closed and open configurations, respectively;

FIGS. 9C and 9D are alternative schematic plan views of the ring of FIG. 9A;

FIG. 10 is a schematic plan view of a ring and attachment tab assembly for use in a catheter fastening mechanism in accordance with one embodiment of the invention;

FIGS. 11A and 11B are schematic top and front views of a fastening strap for use in the catheter fastening mechanism of FIGS. 8A and 8B;

DETAILED DESCRIPTION

In the following, various embodiments of the present invention are described with reference to drainage catheters. It is, however, to be understood that the present invention can also be used with other types of tubular medical devices, as discussed hereinabove.

Figure 1:
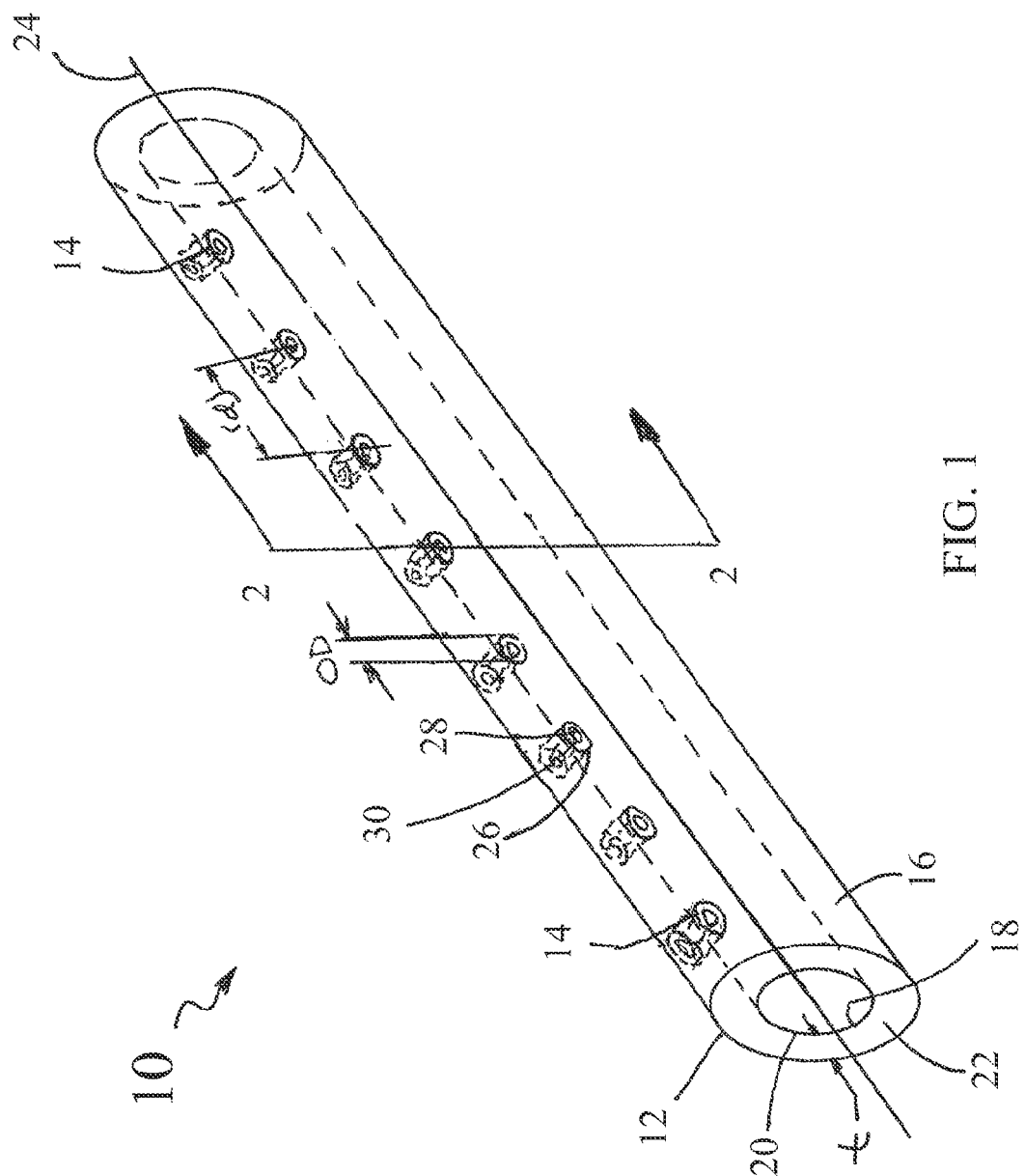
FIG. 1 is a schematic perspective view of a catheter in accordance with one embodiment of the invention.

FIG. 1 is a schematic perspective view of a catheter 10 in accordance with the invention. The catheter 10 includes a first tubular body 12 and at least one second tubular body 14. The first tubular body 12 includes an outer surface 16 and at least one inner surface 18 that defines at least one lumen 20. As shown in FIG. 1, the lumen 20 extends through the entire length of the catheter 10; however, the lumen 20 may only extend partially through the catheter 10 in other embodiments depending on the application of the catheter 10. The first tubular body 12 also includes a wall 22, at least partially defined by the outer surface 16 and the inner surface 18, and a longitudinal axis 24. The first tubular body 12 can be rigid or collapsible.

The second tubular body 14 also includes an outer surface 26 and an inner surface 28 that defines a lumen 30 therethrough. The second tubular body 14 extends through the wall 22 of the first tubular body 12 transversely to the longitudinal axis 24. In some embodiments, the second tubular body is an opening that passes through the wall 22 of the first tubular body 12 without intersecting the lumen 20. The second tubular bodies 14 are shown evenly spaced at a distance (d) along the length of the catheter 10; however, the spacing of the second tubular bodies 14 can vary to suit a particular application. For example, the second tubular bodies 14 may be spaced more closely together at the ends of the catheter 10 (see FIG. 3).

As shown in FIG. 1, the second tubular bodies 14 are disposed on one side of the catheter 10; however, the second tubular bodies 14 can be disposed through the wall 22 of the first tubular body 12 at essentially any radial location with respect to the longitudinal axis 24 (See FIGS. 2A-2F). An outside diameter (OD) of the cross-section of the second tubular body 14 is typically less than a thickness (t) of the wall 22 to prevent intersecting with the lumen 20; however, if the outside diameter of the second tubular body 14 were to exceed the thickness of the wall 22, the outer surface 26 of the second tubular body 14 could be sealed in place to keep the lumens 20, 30 isolated. The second tubular bodies 14 are typically micro-tubes having an inner dimension slightly larger than a cross-section of a suture, tie, needle, or ring that may be used to secure the catheter 10 in place.

Figure 2A:
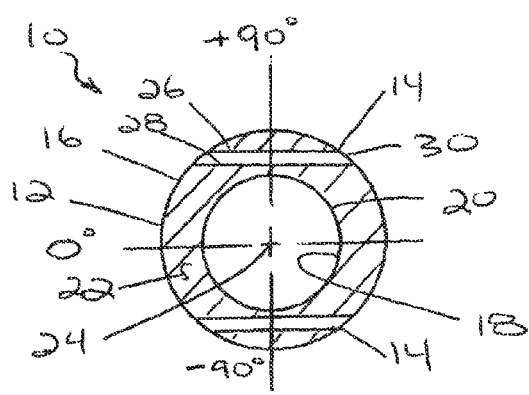
FIG. 2A is a schematic cross-sectional view of the catheter of FIG. 1 taken at line 2-2.

FIG. 2A is a cross-sectional view of the catheter 10 of FIG. 1 taken at line 2-2. As shown in FIG. 2A, the catheter 10 has a generally circular cross-sectional shape; however, the cross-sectional shape can vary to suit a particular application and can be elliptical (FIG. 2C), polygonal (FIG. 2D), or combinations thereof (FIG. 2E). The outer surface 16 and the inner surface 18 are generally concentric with the wall 22 having a substantially constant thickness; however, the thickness of the wall 22 can vary along the length of the catheter 10. In addition, the outer surfaces 16, 26 and the inner surfaces 18, 28 are shown with substantially constant dimensions; however, the outer surfaces 16, 26 and the inner surfaces 18, 28 can also vary dimensionally along a length of the catheter 10. FIG. 1 depicts the second tubular bodies on only one side of the catheter; however, for illustrative purposes, FIG. 2A depicts two second tubular bodies 14 in the cross-section radially oriented 180 degrees apart. Generally, the radial orientation of the second tubular bodies 14 corresponds to a point of intersection between the second tubular body 14 and the wall 22 about the longitudinal axis 24 of the catheter 10.

Figure 2B:
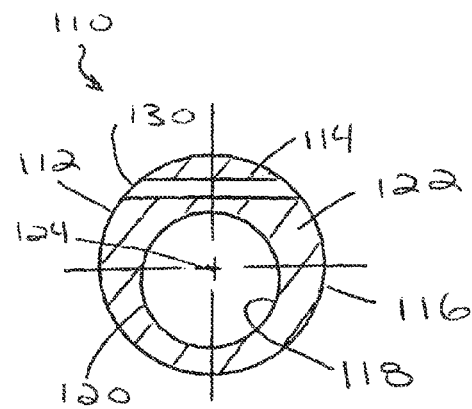
FIGS. 2B to 2F are alternative schematic cross-sectional views of catheters in accordance with various embodiments of the invention.
Figure 2C:
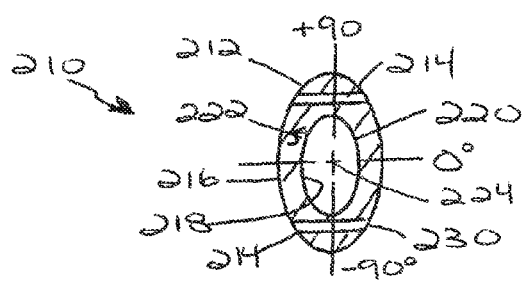
Figure 2D:
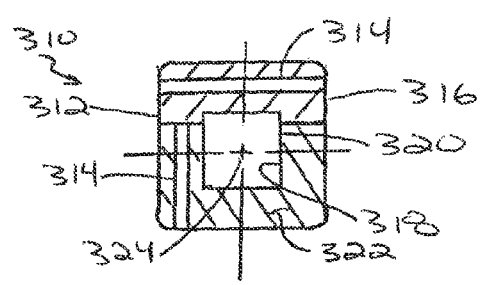
Figure 2E:
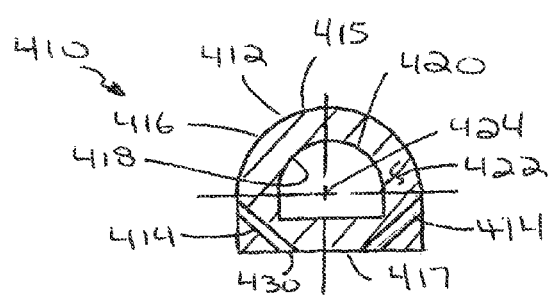

FIGS. 2B-2F depict alternative cross-sections of the catheter 10 of FIG. 1. In FIG. 2B, the outer surface 116 and the inner surface 118 of the first tubular body 112 are eccentric, such that the thickness of the wall 122 is greater on one side than the other. The second tubular body 114 is shown extending through the thicker wall 122, as the greater wall thickness may provide additional reinforcement against the forces arising on the second tubular body 114 when the catheter 110 is secured in place.

FIG. 2C depicts a catheter 210 with an elliptical cross-sectional shape. The catheter 210 includes an outer surface 216 and an inner surface 218 and two second tubular bodies 214 disposed 180 degrees apart. FIG. 2D depicts a catheter 310 with a polygonal cross-sectional shape in split cross-section. The catheter 310 includes an outer surface 316 and an inner surface 318. The catheter 310 is shown in split cross-section so as to depict the two second tubular bodies 314 disposed 90 degrees apart and located at different points along the length of the catheter 310. The catheter 410 shown in FIG. 2E includes circular and polygonal shapes. The outer surface 416 includes an arcuate top portion 415 and a rectangular base portion 417. The inner surface 418 has a substantially similar shape resulting in a substantially constant wall thickness. The catheter 410 includes two second tubular bodies 414 extending through the base portion 417 and disposed about 90 degrees apart relative to the longitudinal axis 424.

Figure 2F:
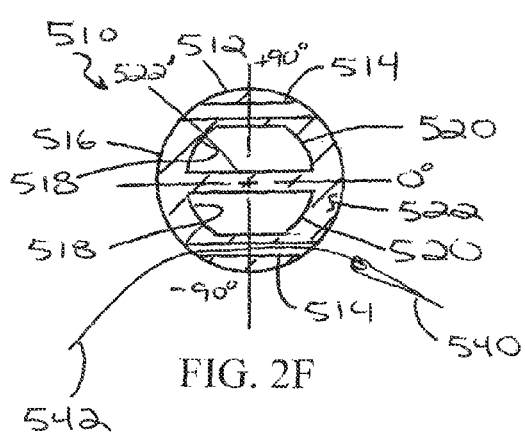

FIG. 2F depicts a catheter 510 with an outer surface 516 and two inner surfaces 518 defining two lumens 520. The catheter 510 includes two second tubular body 514 disposed about 180 degrees apart. The catheter 510 also includes a wall 522' separating the two lumens 520. In one embodiment, a second tubular body 514 can extend through the wall 522'. FIG. 2F also depicts one method of securing the catheter 510. As shown, a needle 540 carrying a suture 542 is passed through one of the second tubular bodies 514. The needle 540 and suture 542 can then be passed through an adjacent bodily structure and the suture 542 tied off to secure the catheter 510 in place.

Figure 3:
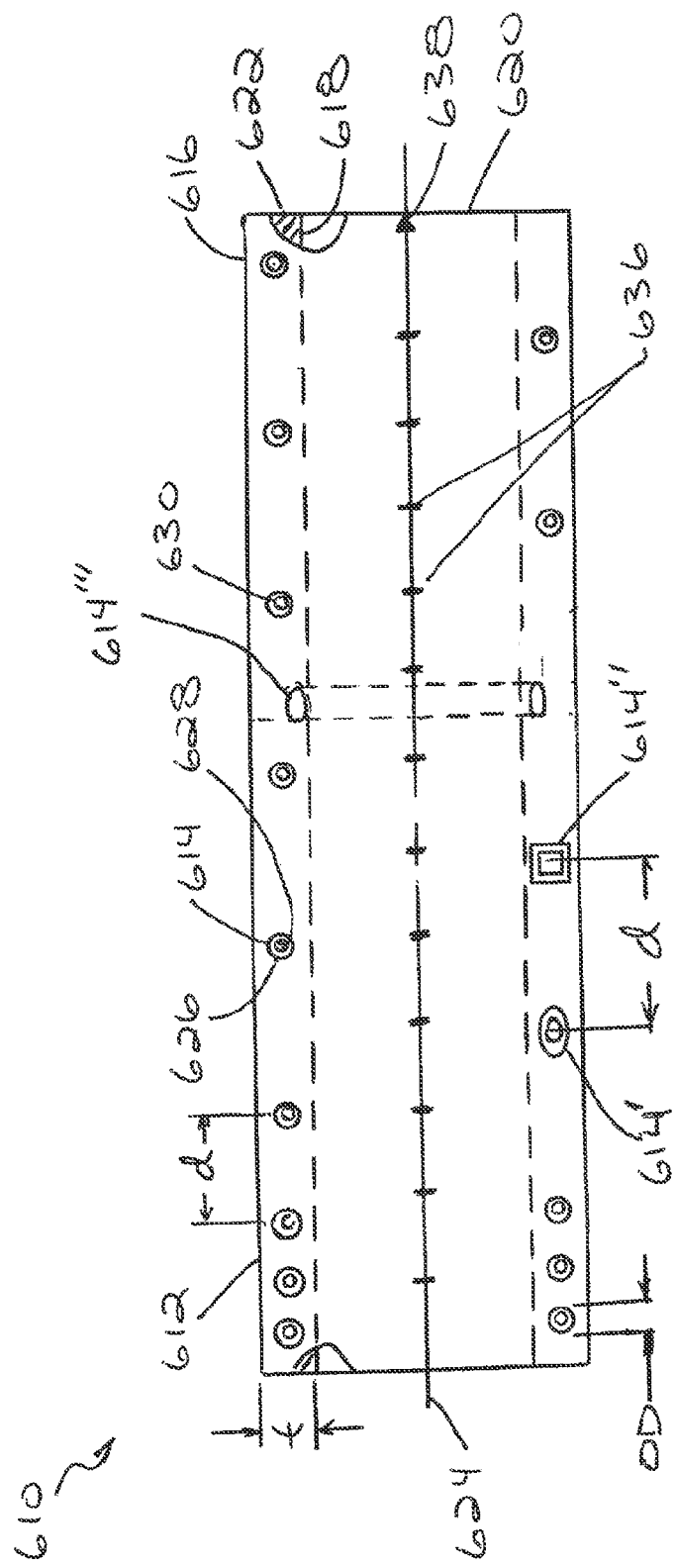
FIG. 3 is a schematic plan view of a catheter in accordance with one embodiment of the invention.

The catheter 610 depicted in FIG. 3 includes a first tubular body 612 having an outer surface 616 and an inner surface 618 defining a lumen 620 and a wall 622. The catheter 610 also includes a plurality of second tubular bodies 614. The cross-sectional shapes of the second tubular bodies 614 can vary depending on the means used to secure the catheter 610 to the patient. As shown in FIG. 3, the cross-sectional shapes can include circular, elliptical (second tubular body 614'), polygonal (second tubular body 614"), and combinations thereof. Additionally, the spacing of the second tubular body 614 can vary along the length of the catheter 610. As shown, the second tubular bodies 614 are located more closely together at the ends of the catheter 610 and then spaced further apart along the body of the catheter 610.

Furthermore, where second tubular bodies 614 are disposed on more than one side of the catheter 610, the second tubular bodies 614 can be staggered to provide greater options for securing the catheter 610. Additionally, one or more second tubular bodies 614''' can be disposed at 90 degrees relative to the longitudinal axis 624 and the other second tubular bodies 614 to provide additional anchoring options. In one embodiment, the spacing and orientation of the second tubular bodies 614 can correspond to the patient's anatomy and/or for the specific application of the catheter 610. Additionally, the catheter 610 can include a series of markings 636 on its outer surface 616. The markings 636 can take the form of numerical or color indicia that medical personal can use to determine size and placement location of the catheter 610. The catheter 610 can also include a radio-opaque material 638 disposed therein to aid in the internal placement of the catheter 610.

Figure 4:
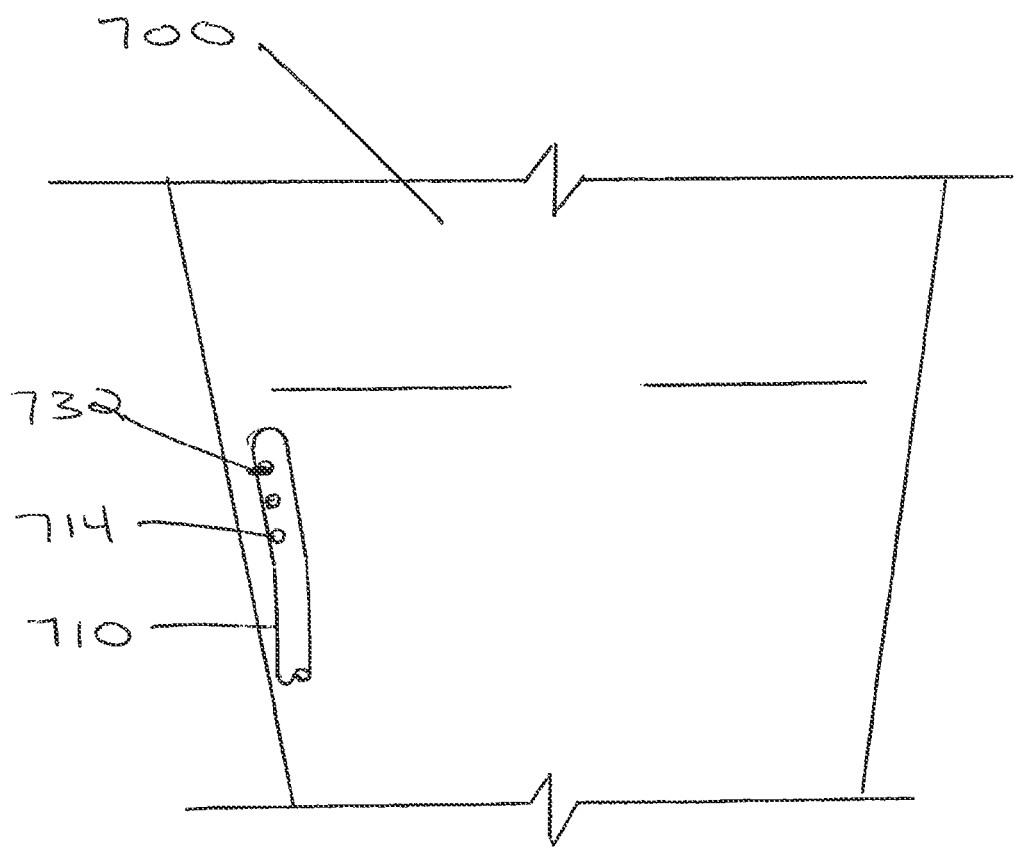
FIG. 4 is a schematic view of a catheter in accordance with one embodiment of the invention secured to a patient.

FIG. 4 depicts one possible application of a catheter 710 in accordance with the invention. As shown, the catheter 710 is used as a chest tube and is secured to the patient 700 by the use of a suture 732. Because the catheter 710 includes a plurality of second tubular bodies 714 located at multiple locations, the physician can choose at which location to secure the catheter 710 that best suits the anatomy of the patient 700 and the application of the catheter 710.

Figure 5:
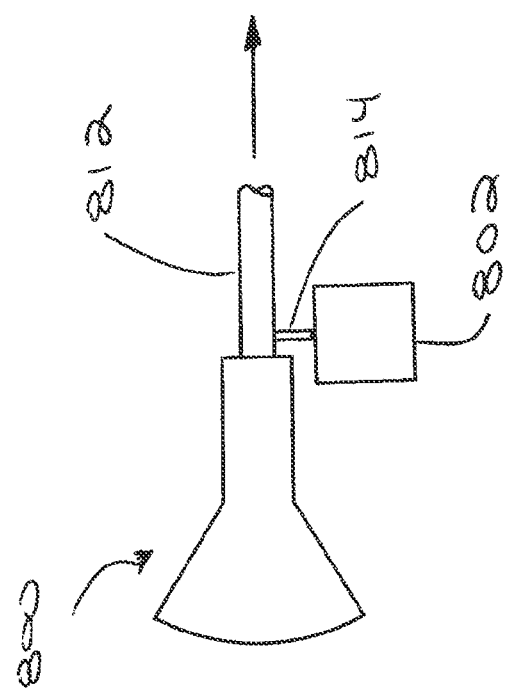
FIG. 5 is a schematic plan view of the manufacturing process of a catheter in accordance with one embodiment of the invention.

FIG. 5 depicts a plan view of an extrusion machine 800 for practicing a method of manufacturing a catheter 810 in accordance with the invention. The machine 800 can be any conventional type of extruder used to extrude or injection mold tubular bodies; for example, the FTX Twin-Screw extruder available from Farrel Corporation of Ansonia, Conn. The first tubular body 812 is extruded from the machine 800. As the first tubular body 812 exits the extruder, a second tubular body 814 is inserted through a wall of the first tubular body 812, either manually or automatically, before the first tubular body 812 has set. The second tubular body 814 may be held by a fixture 802 that performs the insertion step.

The fixture 802 can be fixed to the machine 800 or stand alone. The position of the fixture can 802 can be adjusted to properly align the second tubular body 814 with the first tubular body 812, for example, to prevent the second tubular body 814 from intersecting with a lumen within the first tubular body 812. The fixture 802 may also be adjustable to vary the angle at which the second tubular body 814 is inserted into the first tubular body 812. The fixture 802 can also be rotated to insert the second tubular body 814 at any radial location about the first tubular body 812, or more than one fixture 802 can be used. The fixture 802 may also include drive means, such as, for example, a linear or rotary actuator to drive the second tubular body 814 through the wall of the first tubular body 812. In one example, the second tubular body 814 is driven through the wall of the first tubular body 812 by a hydraulic or pneumatic cylinder. In another embodiment, a mechanical arm drives the second tubular body 814 out of the fixture 802. In one embodiment, the second tubular body 814 is a micro-tube with a sharp leading edge that facilitates insertion of the second tubular body 814 through the wall of the first tubular body 812. As the first tubular body 812 sets (e.g., hardens and/or cures), the second tubular body 814 becomes fixed within the wall of the first tubular body 812.

In additional embodiments, the fixture 802 holds multiple second tubular bodies 814 for insertion along the length of the first tubular body 812 as it is extruded. The fixture 802 can include a hopper for holding the plurality of second tubular bodies 814 or can have means for receiving cartridges holding the second tubular bodies 814. The second tubular bodies 814 can be fed to a firing or insertion location in the fixture 802 by, for example, gravity, magnetic force, cog and wheel, or the like. Once at least one second tubular body 814 is in the firing location, the drive means can drive the second tubular body 814 out of the fixture 802. The drive means can be a reciprocating type actuator that repeatable drives the second tubular bodies 814 out of the fixture 802 and into the first tubular body 812 at, for example, set intervals.

Figure 6:
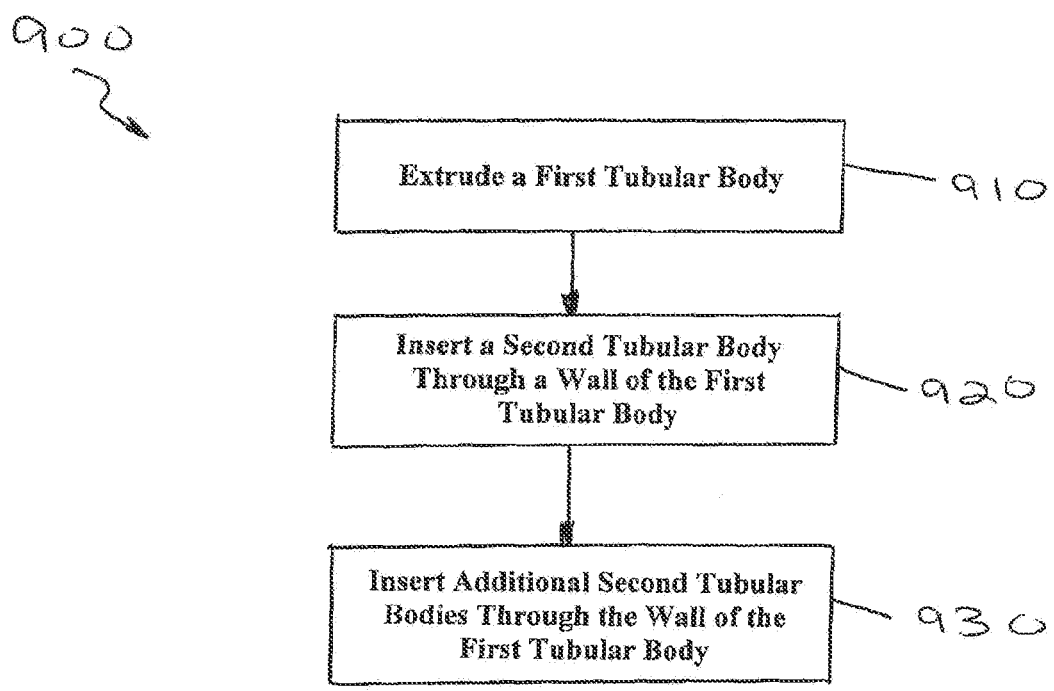
FIG. 6 is a flow chart of a method of manufacturing a catheter in accordance with one embodiment of the invention.

FIG. 6 depicts the steps of the method of manufacturing a catheter in accordance with the invention 900. At step 910, a first tubular body is extruded. A second tubular body is inserted through a wall of the first tubular body at step 920. The second tubular body is inserted as the first tubular body is extruded and before the first tubular body has set. The method 900 includes optional step 930, where additional second tubular bodies are inserted through the first tubular body.

The size and shape of the catheter will vary to suit a particular application (e.g., feeding tube or drainage catheter) and patient (e.g., adult or pediatric). For example, the catheter can have a length from about 5 cm to about 180 cm, preferably about 10 cm to about 150 cm, and more preferably about 15 cm to about 120 cm. The diameter of the catheter can range from about 0.5 mm to about 20 mm or from 1 French to about 40 French. The size, shape, and placement of the second tubular bodies can also vary to suit a particular application; however, because the catheters in accordance with the invention are universal in nature, the second tubular bodies may be evenly spaced along the length of the catheter and/or radially about the catheter. The spacing of the second tubular bodies will generally correspond to the overall size of the catheter and its application. For example, for a 30 cm long chest tube, the second tubular bodies may be spaced every 2 cm along the length of the catheter. The inner diameter of the second tubular bodies will also vary to suit a particular application, including the method of securing the catheter in place; however, the maximum diameter of the inner diameter may be limited to reduce movement of the secured catheter by virtue of the clearance between the securing means and the inside diameter of the second tubular body.

Generally, the catheters can be manufactured by injection molding or by modifying an extruded tube. For example, extrusion can be used to provide a uniform polymeric tube, to which other components are attached, for example hubs or valves. Insert molding can then be used to provide the desired geometry of the perforation, or the perforations can be created in the desired locations as a subsequent mechanical operation.

The catheters and related components can be manufactured of biocompatible materials, such as, for example, polyurethane, silicones, polyethylenes, nylons, polyesters and polyester elastomers, either with or without reinforcement. Stainless steel and titanium can also be used, for example, for the micro-tubes. In one example, the catheter is polyurethane (e.g., Tecoflex, available from Thermedics, Woburn, Mass.). Also, the polymeric materials may be used in combination with other materials, for example, natural or synthetic rubber. Other suitable materials will be apparent to those skilled in the art. In addition, the catheter, or portions thereof, can include an echogenic coating for ultrasound imaging.

Figure 7B:
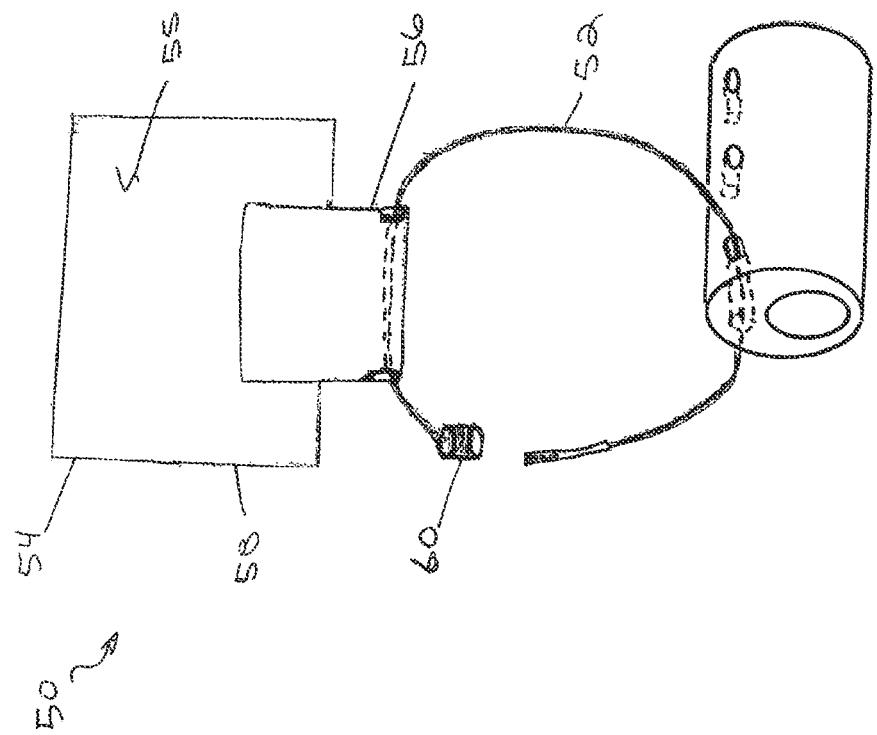
FIG. 7B is a schematic plan view of the catheter fastening mechanism of FIG. 7A.
Figure 7A:
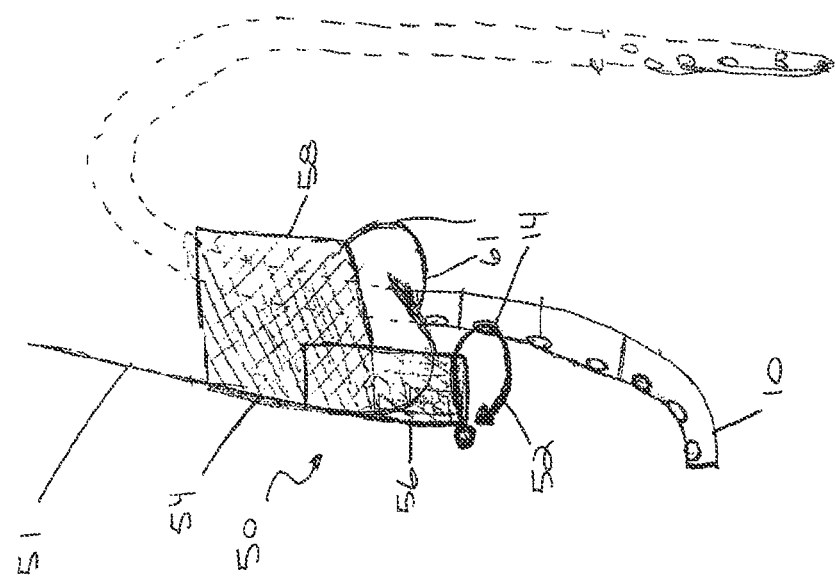
FIG. 7A is a schematic perspective view of a catheter secured to a mammalian body by a catheter fastening mechanism in accordance with one embodiment of the invention.
Figure 7C:
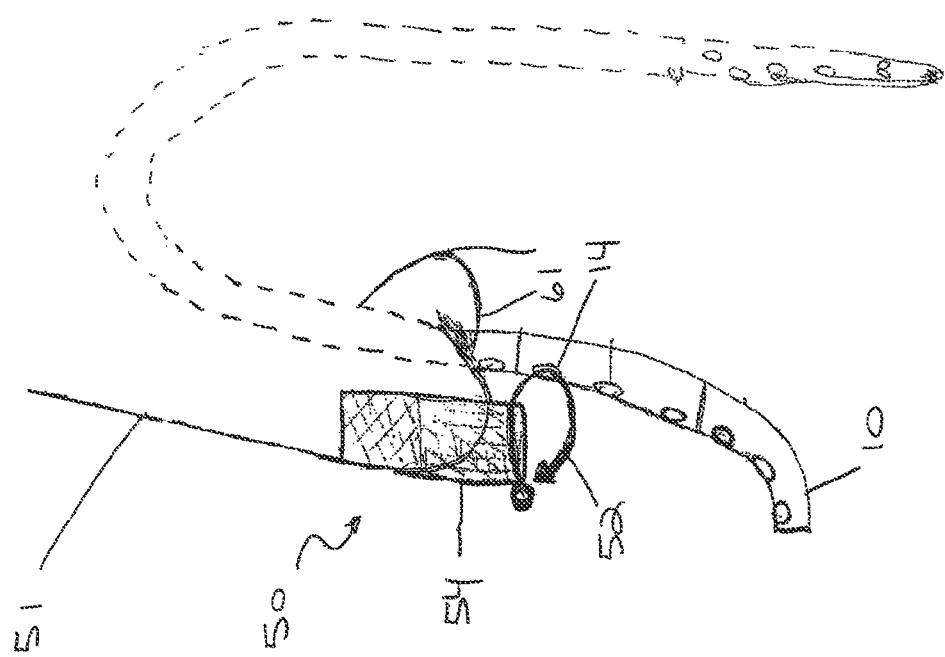
FIG. 7C is a schematic perspective view of a catheter secured to a mammalian body by a catheter fastening mechanism in accordance with an alternative embodiment of the invention.
Figure 8A:
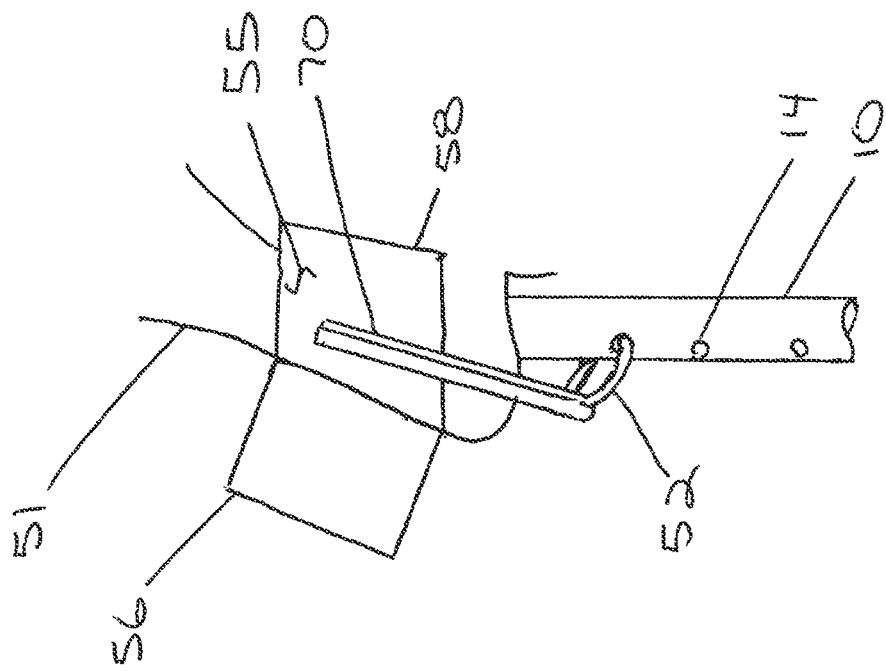
FIGS. 8A and 8B are schematic front and side views of a catheter secured to a mammalian body by a catheter fastening mechanism in accordance with an alternative embodiment of the invention.
Figure 8B:
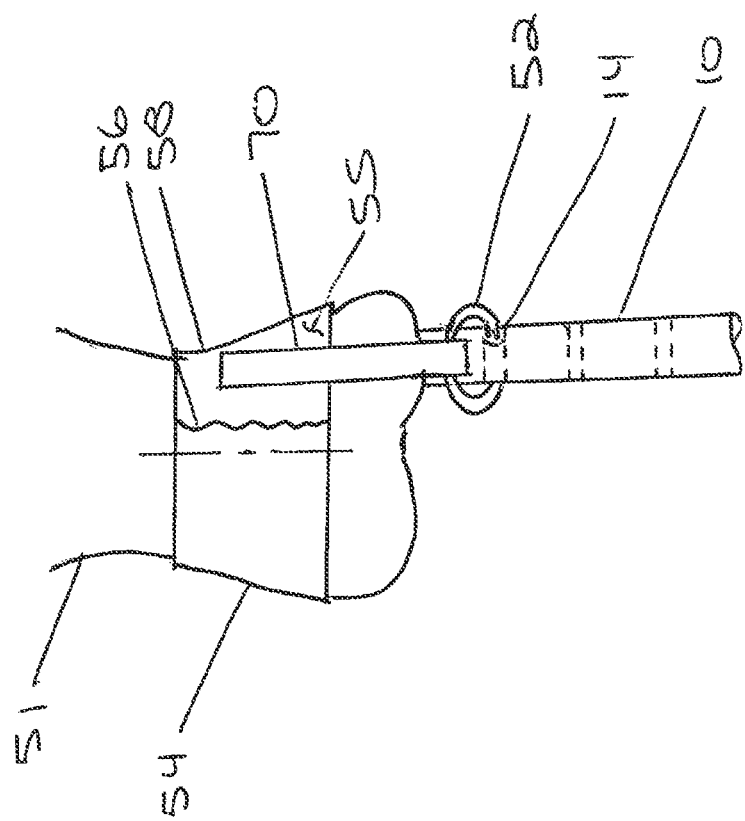

FIGS. 7A and 7B depict one embodiment of a catheter fastening mechanism 50. The mechanism 50 can be used with any of the catheters 10 described herein; however, the mechanism 50 is not limited to use with those specific catheters. The mechanism 50 depicted in FIGS. 7A and 7B is a suspension device for a nasogastric suction tube. FIGS. 7C, 8A, and 8B depict alternative embodiments of the mechanism 50. Generally, the various embodiments of the mechanism 50 include a ring 52 (see, for example, FIGS. 9A and 9B) that engages an opening 14 in the tube 10 and is secured to the body by a fastening strap 54 (see, for example, FIGS. 11A and 11B). The use of the ring 52 and strap 54 arrangement provides a "floating" connection of the catheter to the patient's body, allowing some minor movement of the catheter relative to the patient without the catheter becoming dislodged or being subjected to excessive force. In this particular embodiment, the tube 10 includes openings or micro-tubes 14 spaced about 1 cm apart and oriented approximately 90 degrees to the main lumen 20 of the tube 10.

In practice, the nasogastric tube 10 with its openings 14 running at right angles to the main lumen is inserted into the body to an appropriate level. At least a portion of the fastening strap 54, which may include one or more layers/pieces of material, is placed on the bridge of the patient's nose 51. At least one ring 52 is passed through the opening 14 at an appropriate level for the patient and application, in this case about 1 cm to about 3 cm from the external nares 61. In the embodiment shown, the ring 52 is opened so that one end thereof can be passed through the opening 14 in the tube 10; however, the tube 10 can be manufactured with solid rings installed at predetermined locations on the tube 10. In the embodiment shown, the ring 52 includes a locking mechanism 60, as described in greater detail hereinbelow. Depending on the application, additional rings 52 and/or fastening straps 54 can be used (see, for example, FIG. 13). The ring(s) 52 is secured to the patient via at least another portion of the fastening strap 54. The specific manner of attachment is described later with respect to FIGS. 7A-7C, 8A, and 8B.

The ring 52 is shown in the closed configuration in FIG. 9A and the open configuration in FIG. 9B. In the embodiment shown, the ring 52 has a generally circular configuration and is biased into the open position by, for example, spring tension in the body of the ring 52 (i.e., the tendency of the bent ring to try to return to an unbent configuration). Alternatively, the ring 52 can be manufactured with a set gap between the ends thereof, where the gap is closed by the locking mechanism 60 or crimping the ends together. In addition, the term ring is used herein to include similar structures, such as loops or hooks, which may include shapes such as, for example, C, J, S, U, and Z. The ring 52 can be made of a metal or plastic material. In one embodiment, the ring 52 has an outside diameter of about 1 cm to about 5 cm and the body (e.g., wire diameter) of the ring 52 has a cross-sectional dimension of about 2 mm to about 8 mm.

The locking mechanism 60 for the ring 52 is intended to hold the ends of the ring 52 together and prevent the inadvertent decoupling of the ring 52 and the tube 10. The locking mechanism 60 can have various arrangements. As shown in FIG. 9B, the mechanism 60 includes an internally threaded collar 62 crimped on one end of the ring 52 and a threaded portion 64 disposed on the other end of the ring 52. Alternative locking mechanisms are also possible, such as, for example, box clasps, toggle clasps, hook and eye clasps, friction clasps, and magnetic clasps. Essentially any locking mechanism can be used providing that the portion of the mechanism that passes through the opening 14 is smaller in circumference than that of the opening 14. In one embodiment, the ring 52 can include a sharpened tip configured to pierce through a wall of a catheter where no openings are provided; however, due care should be exercised to avoid breaching the lumen of the catheter and rendering the catheter unfit for its intended application.

FIGS. 9C and 9D depict alternative ring configurations. As shown in FIG. 9C, the ring 152 has a substantially oval or elliptical shape and includes a locking mechanism 160 of the types previously described. FIG. 9D depicts a ring 252 having a rectangular configuration, although other polygonal shapes are also contemplated and within the scope of the invention. The ring 252 includes a locking mechanism 260 having a simple bar and U mechanism or friction fit.

Generally, the size and shape of the fastening strap 54 will vary to suit a particular application and will depend, for example, on the type of catheter to be secured and the location where the catheter is to be secured. The strap 54 shown in FIGS. 7A, 7B, 8A, and 8B has a generally rectangular shape; however, the shape of the strap 54 may be tailored by cutting with scissors. The strap 54 can be manufactured from a porous or non-porous material including, for example, a woven cloth material of natural and/or synthetic fibers.

In one embodiment, the strap 54 includes two layers 56, 58 with a lower or first layer 58 usually placed first. The first layer 58 includes a lower surface 59 (see, for example, FIG. 11B) that can include an adhesive material deposited thereon. The lower surface 59 may include a removable covering 53 to isolate the adhesive material from the environment until ready to use. The covering 53 can be removed from all or a portion of the lower surface 59 and the lower surface 59 applied to the patient's skin. The skin may be prepped with Mastisol® brand liquid adhesive, as available from Ferndale Laboratories, Inc., prior to applying the first layer 58. The first layer 58 can include an adhesive or hook and loop type fastener on its upper surface 55. The upper surface 55 can also include a covering 53 to prevent contamination of the upper surface 55. The covering 53 can be removed from all or a portion of the upper surface 55 prior to use.

The upper or second layer 56 of the strap 54 can be bonded firmly or otherwise attached to the first layer 58. For example, as shown in FIG. 11B, the second layer 56 can be attached to the first layer 58 proximate a midline 65 of the first layer 58 over its vertical length and for a width of about ½ cm to about ¾ cm. Alternatively, and as shown in FIGS. 7A and 7B, the first and second layers 58, 56 can be attached in an overlapping manner. The second layer 56 can have an adhesive or hook and loop type fastener disposed on a lower surface 57 thereof to securely interface with the upper surface 55 of the first layer 58. The adhesive or hook and loop type fastener can extend over the entire lower surface 57, except in the embodiment of FIGS. 11A and 11B, where the second layer 56 is bonded to the first layer 58 at the midline. The use of a hook and loop type fastener allows the first and second layers 58, 56 to be repositioned relative to one another.

As shown in FIGS. 7A and 7B, the ring 52 is attached to the second layer 56 of the fastening strap 54, which acts as a holding strip for the ring 52. In the embodiment shown, the second layer 56 is slightly smaller than the first layer 58; however, the size and shape of the second layer 56 will vary to suit a particular application. In one embodiment, the first layer measures from about 4 cm to about 7 cm in width and about 3 cm to about 4 cm in length and the second layer measures from about ½ cm to about ¾ cm in width and about 2 cm to about 4 cm in length for a nasogastric tube application. The second layer 56 depicted in FIGS. 7A and 7B can include one side coated with an adhesive and optionally covered by a peel off strip with a tab (i.e., covering 53). In one embodiment, the second layer 56 is folded over a portion of the ring 52 and the side coated with the adhesive secured to itself, thereby gripping the ring 52. The opposing side, now the outer surface of the folded second layer 56, can also include an adhesive coating or a hook and loop type fastener on at least a portion thereof. The second layer 56 can now be secured to the first layer 58 of the fastening strap 54 previously secured to the patient's skin via the adhesive coating or mating hook and loop type fasteners, thereby securing the tube 10 in place. Alternatively, the second layer 58 can be applied to the patient's skin at the same time as the first layer 58 is applied and can be sandwiched between the first layer 58 and the patient's skin. As shown in FIG. 7B, the second layer 56 does not align evenly with the first layer 58, but extends beyond the first layer by, for example, about 1 to 2 cm.

In the alternative embodiment shown in FIG. 7C, the fastening strap 54 includes only a single layer (e.g., second layer 56). In this arrangement, the tube 10 is first inserted into the patient at the appropriate position and then the fastening strap 54 and ring 52 assembly is secured to the patient. The fastening strap 54 can be trimmed as needed to suit the application site and the covering 53 removed to expose the adhesive coating. The patient's skin can be prepped as previously described. The fastening strap 54 is secured to the patient's skin and the attached ring 52 is passed through the appropriate opening 14.

The catheter fastening mechanism 50 shown in FIGS. 8A and 8B utilizes the fastening strap 54 shown in greater detail in FIGS. 11A and 11B. In addition to the fastening strap 54 having two substantially evenly aligned layers 56, 58, the mechanism 50 includes an additional holding tab 70 (see FIG. 10). As shown in FIG. 10, the holding tab 70 is secured at one end 72 to the ring 52. In one embodiment, the strap end 72 is folded over the body of the ring 52 and secured to itself by, for example, adhesive or stitching. In the embodiment shown in FIG. 10, the holding tab 70 measures about 3 cm to about 6 cm in length, about 0.5 cm in width, and about 2 mm in thickness, however, the size and shape of the tab 70 will vary to suit a particular application. The holding tab 70 and ring 52 are sized and configured such that the tab 70 can be secured to the ring 52 prior to inserting the ring 52 through the opening 14 in the catheter 10 or thereafter. The holding tab 70 can include an adhesive or hook and loop type fasteners on one or both sides thereof.

As shown in FIGS. 8A and 8B, the first layer 58 of the fastening strap 54 is secured to the patient's nose 51. At least a portion of the holding tab 70 is positioned over the first layer 58. In the embodiment shown in FIG. 8A, the ring 52 is inserted through the opening 14 in the tube 10 prior to positioning over the first layer 58 of the fastening strap 54. The holding tab 70 may be held in position by the adhesive or mating hook and loop fasteners disposed on the holding tab 70 and the upper surface 55 of the first layer 58. The second layer 56 of the fastening strap 54 is then positioned over the first layer 58, thereby sandwiching the holding tab 70 between the two layers 56, 58.

Figure 12A:
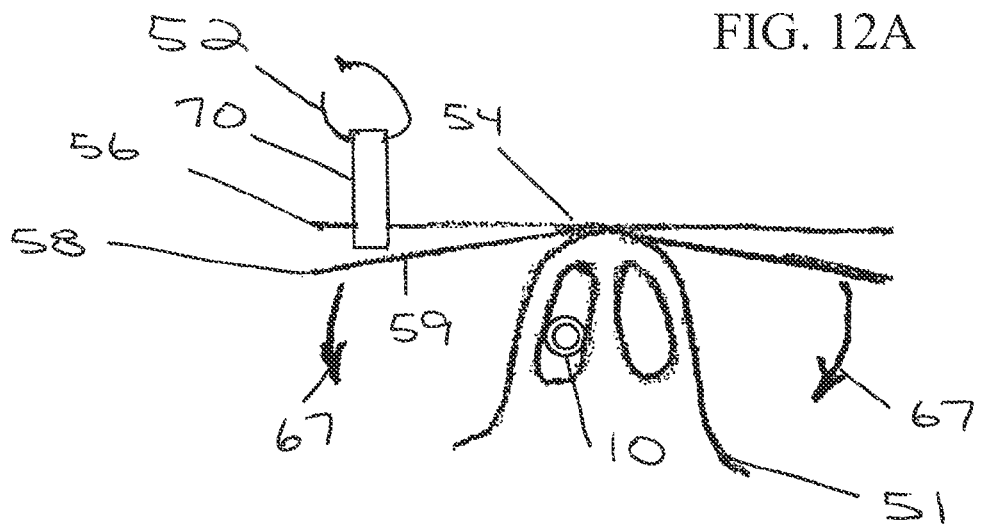
FIGS. 12A and 12B are schematic plan views depicting the installation of a catheter fastening mechanism in accordance with one embodiment of the invention.
Figure 12B:

FIGS. 12A and 12B further depict the installation of the catheter fastening mechanism 50 of FIGS. 8A and 8B using the fastening strap 54 depicted on FIGS. 11A and 11B. As previously described, the fastening strap 54 includes first and second layers 58, 56 connected proximate their midline 65. The strap 54 is positioned on the patient's nose 51. The first layer 58 is pressed onto the patient's nose 51 (arrows 67), allowing the adhesive covered lower surface 59 of the first layer 58 to contact the patient's skin.

Subsequently, the covering 53 can be removed from the side of the upper surface 55 of the first layer 58 corresponding to the nostril in which the tube 10 is inserted, thereby exposing the adhesive or hook and loop type fastener. The holding tab 70 is positioned over the first layer 58 on the exposed side. The portion of the second layer 56 corresponding to the side where the holding tab 70 is positioned is then attached (for example, by adhesive or hook and loop type fastener) to the upper surface 55 of the first layer 58, thereby securing the tab 70 between the two layers 56, 58. Where the second layer 56 includes a covering on its lower surface 57, the covering 53 can be removed as needed to expose the adhesive or hook and loop type fastener for securing to the upper surface 55 of the first layer 58.

Alternatively, in an application not using the holding tab 70, at least a portion of the second layer 56 can be passed through the ring 52, which may or may not be secured to the tube 10 at this point. The portion of the second layer 56 that is passed through the ring 52 will depend on which nostril the tube 10 is inserted. The second layer 56 can then be secured to the upper surface 55 of the first layer 58, as previously described.

Figure 13:
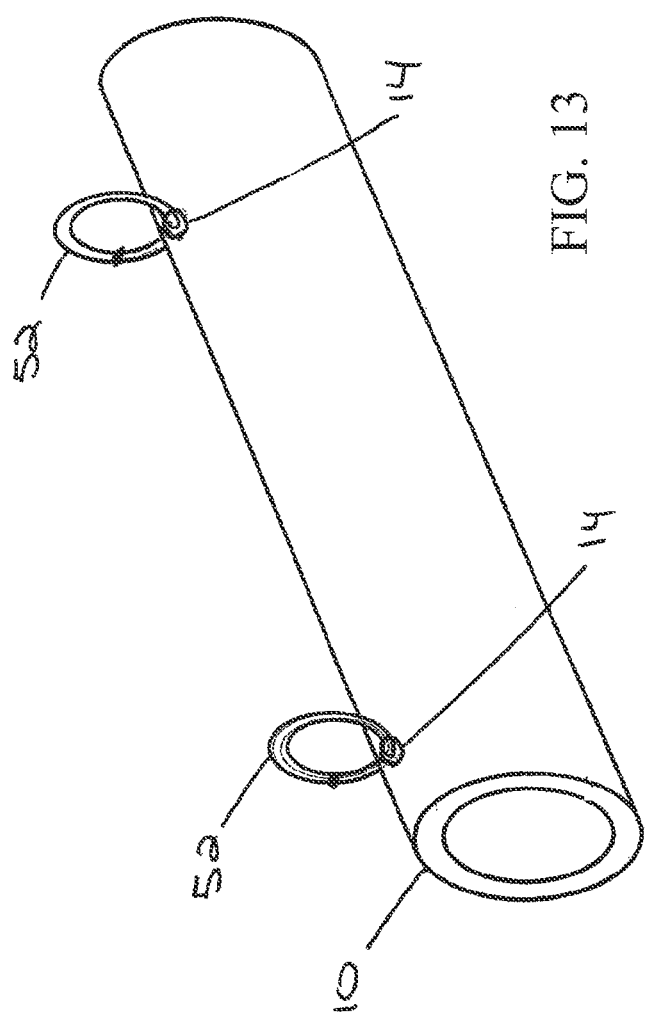
FIG. 13 is a schematic perspective view of an alternative arrangement of a catheter and fastening rings in accordance with one embodiment of the invention.

FIG. 13 depicts an alternative arrangement of a catheter fastening mechanism in accordance with one embodiment of the invention. As shown, the catheter 10 includes multiple rings 52 secured along the length of the catheter 10. Multiple rings 52 can be used to provide more than one fastening point for securing the catheter 10. Additionally or alternatively, sutures could be used to secure the rings 52 to the patient, either with or in place of the fastening strap.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

What is claimed is:

1. A method of securing a catheter in a mammal, the method comprising the steps of:
   (a) inserting at least a portion of the catheter into a predetermined region of the mammal, the catheter comprising:
      (i) a first tubular body comprising:
         an outer surface;
         an inner surface defining a lumen extending longitudinally at least partially through a length of the tubular body;
         a wall at least partially defined by the outer surface and the inner surface; and
         a longitudinal axis; and
      (ii) at least one second tubular body comprising:
         an outer surface;
         an inner surface defining a lumen extending longitudinally through the at least one second tubular body; and
         a wall at least partially defined by the outer surface and the inner surface, wherein the at least one second tubular body is disposed through the wall of the first tubular body transversely to the longitudinal axis and substantially flush with the outer surface of the first tubular body,
      wherein the catheter is inserted into the mammal so that at least one second tubular body is located outside the predetermined region; and
   (b) securing the catheter to an anatomical structure of the mammal via a fastening mechanism, the fastening mechanism comprising:
      (i) a ring having opposed free ends and constructed and arranged so that the ring can assume one of an open configuration and a closed configuration;
      (ii) a locking mechanism to reversibly secure the ring in the closed configuration and including mating first and second locking members that are respectively supported at the opposed free ends of the ring; and
      (iii) a strap member for coupling the ring to the anatomical structure,
      wherein the catheter is secured to the anatomical structure by passing the ring in the open configuration through the lumen of the at least one second tubular body located outside the predetermined region, locking the ring in the closed configuration using the locking mechanism, and coupling the ring to the anatomical structure via the strap member.

2. The method of claim 1, wherein the predetermined region is a body cavity or an organ system.

3. The method of claim 1, wherein the anatomical structure comprises skin or tissue spaced apart from the predetermined region.

4. The method of claim 1, wherein an outer cross-sectional dimension of the at least one second tubular body is less than a thickness of the wall of the first tubular body.

5. The method of claim 1, wherein the at least one second tubular body comprises a plurality of second tubular bodies.

6. The method of claim 1, wherein a cross-sectional dimension of the inner surface of the at least one second tubular body comprises a diameter of about 0.1 mm to about 5.0 mm.

7. The method of claim 1, wherein the outer surface of the first tubular body and the inner surface of the first tubular body are eccentric.

8. The method of claim 1, wherein the first tubular body comprises a material selected from the group consisting of polyurethane, silicone, polyethylene, nylon, polyester, and elastomer.

9. The method of claim 1, wherein the at least one second tubular body comprises a material selected from the group consisting of stainless steel, titanium, polyurethane, silicone, polyethylene, nylon, polyester, and elastomer.

10. The method of claim 1, wherein the catheter comprises a cross-sectional shape selected from the group consisting of circular, elliptical, polygonal, and combinations thereof.

11. The method of claim 1, wherein a cross-sectional shape of the inner surface of the at least one second tubular body is at least one of circular, elliptical, polygonal, and combinations thereof.

12. The method of claim 1, wherein the catheter further comprises a radio-opaque material disposed therein.

13. The method of claim 1, wherein the catheter further comprises a series of markings disposed on the outer surface of the first tubular body.

14. A method of securing a catheter in a mammal, the method comprising the steps of:
(a) inserting at least a portion of the catheter into a predetermined region of the mammal, the catheter comprising:
a tubular body comprising:
(i) an outer surface;
(ii) an inner surface defining a lumen extending longitudinally at least partially through a length of the tubular body;
(iii) a wall at least partially defined by the outer surface and the inner surface;
(iv) a longitudinal axis; and
(v) at least one opening extending through the wall substantially transversely to the longitudinal axis, wherein the at least one opening is in fluidic isolation from the lumen,
wherein the catheter is inserted into the mammal so that at least one opening is located outside the predetermined region; and
(b) securing the catheter to an anatomical structure of the mammal via a fastening mechanism, the fastening mechanism comprising:
(i) a ring having opposed free ends and constructed and arranged so that the ring can assume one of an open configuration and a closed configuration;
(ii) a locking mechanism to reversibly secure the ring in the closed configuration and including mating first and second locking members that are respectively supported at the opposed free ends of the ring; and
(iii) a strap member for coupling the ring to the anatomical structure,
wherein the catheter is secured to the anatomical structure by passing the ring in the open configuration through the at least one opening located outside the predetermined region, locking the ring in the closed configuration using the locking mechanism, and coupling the ring to the anatomical structure via the strap member.

15. The method of claim 14, wherein the predetermined region is a body cavity or an organ system.

16. The method of claim 14, wherein the anatomical structure comprises skin or tissue spaced apart from the predetermined region.

17. The method of claim 14, wherein the step of coupling the ring to the anatomical structure comprises:
attaching the strap member to the anatomical structure using a first layer of material of the strap member; and
securing at least a portion of the ring to the strap member using a second layer of material of the strap member.

18. The method of claim 14, wherein the strap member is adapted to provide a floating connection of the catheter to the mammal.

19. The method of claim 14, wherein the locking mechanism comprises at least one of a box clasp, a toggle clasp, a hook and eye clasp, a friction clasp, and a magnetic clasp.

* * * * *